United States Patent [19]

Cieslak et al.

[11] 4,441,483

[45] * Apr. 10, 1984

[54] PORTABLE FURNACE FOR WEARING APPAREL

[76] Inventors: Stanley Cieslak, 14 Creek Rd.; Leonard K. Cieslak, 15 Creek Rd., both of McKees Rocks, Pa. 15136

[*] Notice: The portion of the term of this patent subsequent to Jan. 1, 1997 has been disclaimed.

[21] Appl. No.: 343,151

[22] Filed: Jan. 27, 1982

Related U.S. Application Data

[63] Continuation-in-part of Ser. No. 186,954, Sep. 15, 1980, Pat. No. 4,334,519, which is a continuation-in-part of Ser. No. 49,059, Jun. 18, 1979, Pat. No. 4,281,418, which is a continuation-in-part of Ser. No. 875,815, Feb. 7, 1978, Pat. No. 4,180,922.

[51] Int. Cl.$^3$ .................................................. A61F 7/00
[52] U.S. Cl. ...................................... 126/206; 126/204; 36/2.6
[58] Field of Search ................ 126/204, 206, 210; D23/78; 422/126; 36/2.6

[56] References Cited

U.S. PATENT DOCUMENTS

| 566,662 | 8/1896 | Cochrane | 126/206 |
|---|---|---|---|
| 912,527 | 2/1909 | Batter . | |
| 1,162,682 | 11/1915 | Cherry | 422/126 |
| 2,648,325 | 8/1953 | Siple | 126/204 |
| 3,547,100 | 12/1970 | Usui | 126/206 |
| 3,572,314 | 3/1971 | Teague, Jr. | 126/210 |
| 3,712,288 | 1/1973 | Weiss | 126/204 |
| 3,793,643 | 2/1974 | Kinoshita | 2/66 |
| 3,874,365 | 4/1975 | Pava | 126/263 |
| 4,180,922 | 1/1980 | Cieslak et al. | 126/263 |
| 4,281,418 | 8/1981 | Cieslak et al. | 2/160 |

FOREIGN PATENT DOCUMENTS

| 587394 | 10/1933 | Fed. Rep. of Germany | 126/204 |
|---|---|---|---|
| 477277 | 6/1953 | Italy | 126/210 |
| 366362 | 2/1932 | United Kingdom | 126/204 |

*Primary Examiner*—Samuel Scott
*Assistant Examiner*—Allen Flanigan
*Attorney, Agent, or Firm*—Carothers & Carothers

[57] ABSTRACT

A portable furnace for generating and circulating heat in wearing apparel. The furnace consists of a compact closed container for containing a liquid therein and a second container is received in the closed container and adapted to receive a heating element therein through an opening to the exterior. At least a portion of the exterior walls of the second container are exposed to the interiors of the compact container for heat transfer through the walls to a liquid contained within the compact container. A flexible liquid conduit has both ends thereof connected for circulation of heated liquid from the container through the conduit and a positive displacement pump is connected to the conduit for hand manipulation to circulate heated liquid from the compact container through the conduit on demand.

8 Claims, 9 Drawing Figures

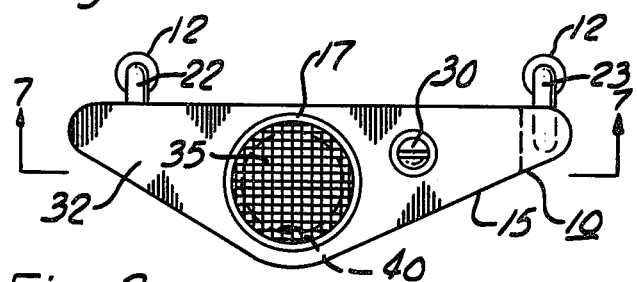
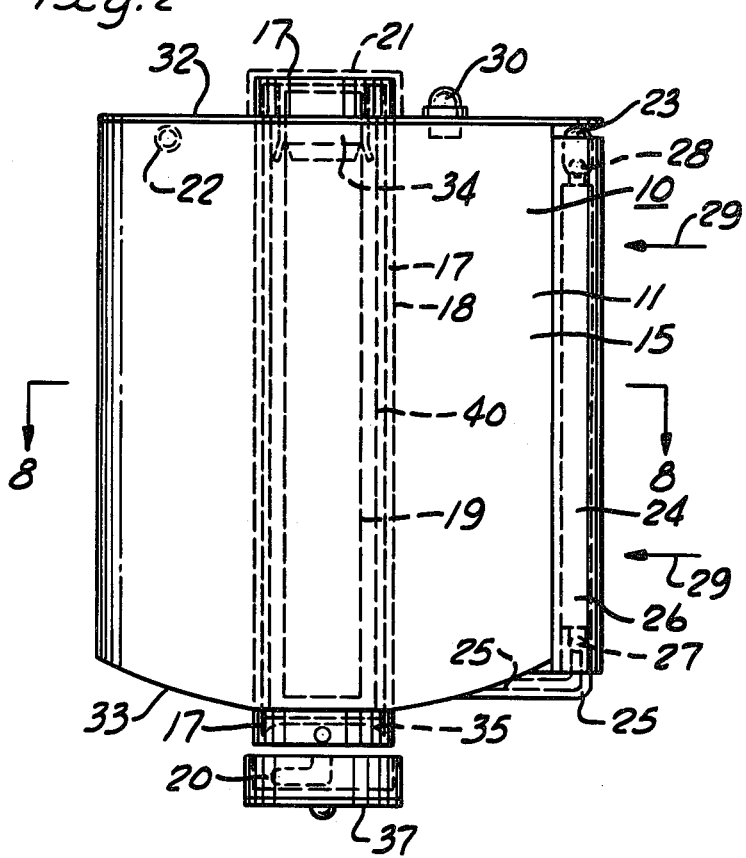
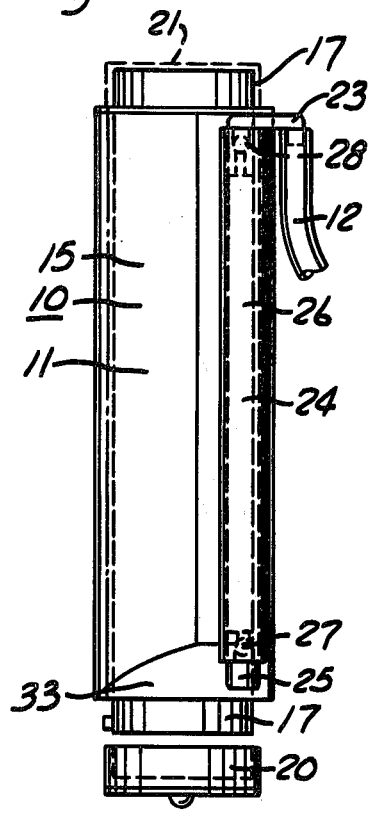
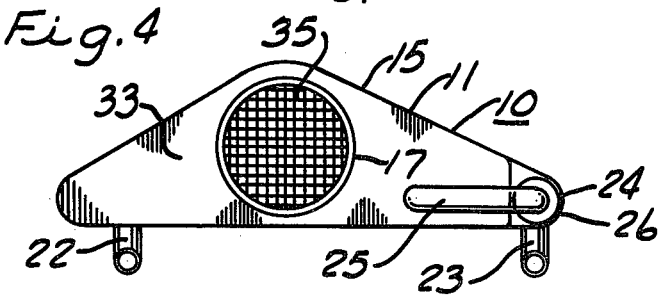
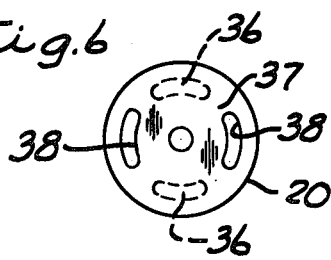

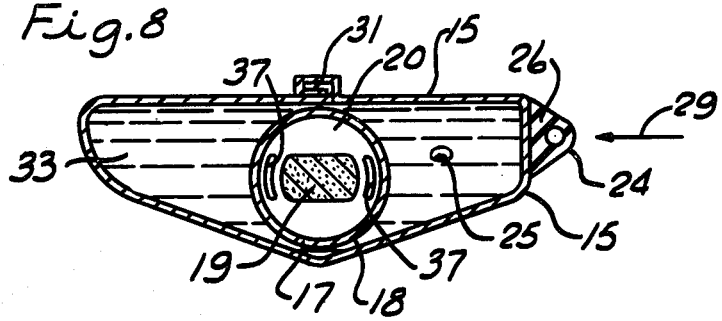
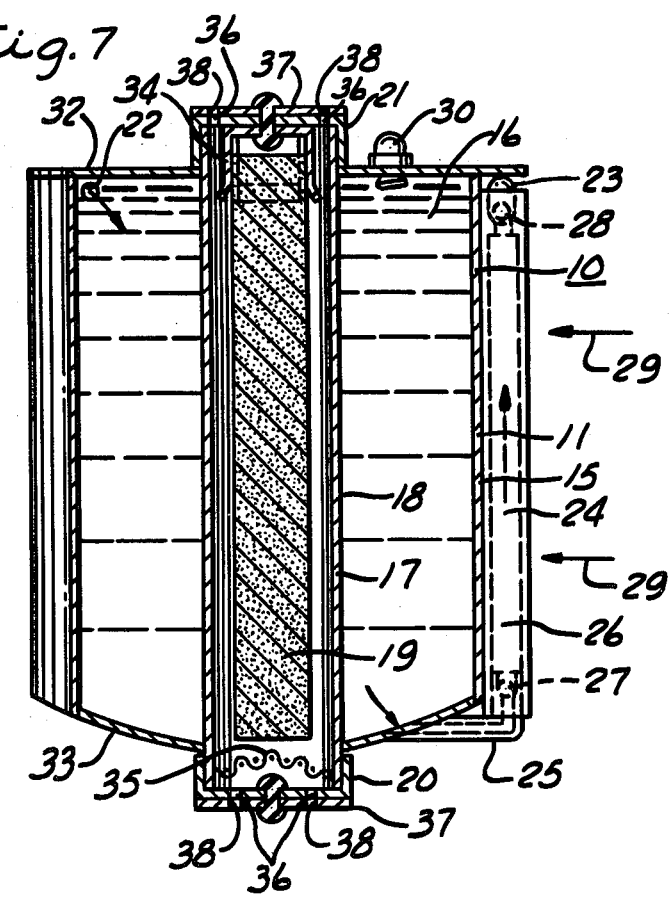
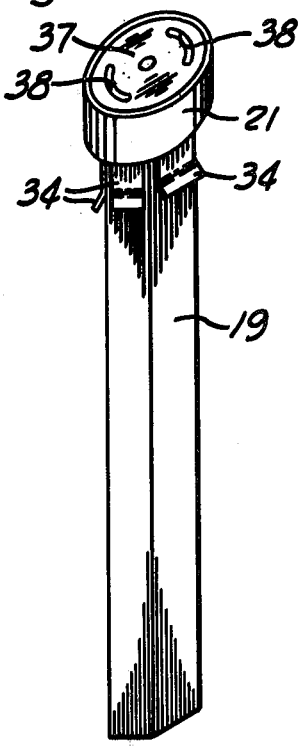

PORTABLE FURNACE FOR WEARING APPAREL

CROSS REFERENCE TO RELATED APPLICATION

This application is a continuation-in-part of U.S. application Ser. No. 186,954, filed Sept. 15, 1980, now U.S. Pat. No. 4,334,519, which is a continuation-in-part of U.S. application Ser. No. 49,059, filed June 18, 1979, now U.S. Pat. No. 4,281,418, which is a continuation-in-part of U.S. application Ser. No. 875,815, filed Feb. 7, 1978, now U.S. Pat. No. 4,180,922.

BACKGROUND OF THE INVENTION

The present invention relates to portable furnaces, and more particularly to compact furnaces or warmers to be carried on the person for circulating heat in wearing apparel such as gloves or boots.

The portable furnace of the present invention pertains to improvements on the portable furnaces illustrated in our U.S. Pat. Nos. 4,180,922 and 4,281,418, issued Jan. 1, 1980 and Aug. 4, 1981, respectively. The present invention further pertains to an improvement on the portable heater illustrated in our co-pending U.S. application Ser. No. 186,954 filed Sept. 15, 1980 now U.S. Pat. No. 4,334,519. The furnaces or heaters illustrated in these disclosures have proved to be efficient and practical. However, it is a principal object of the present invention to provide a portable heater which is less expensive to manufacture, easier to manufacture, and provides even more efficient heat exchange.

SUMMARY OF THE INVENTION

The portable heater or furnace of the present invention for heating wearing apparel or the like generally comprises a compact, closed container for containing a liquid therein, which container is capable of being readily carried on one's person. A second and smaller container is received within this first-mentioned closed liquid container and is adapted to receive a heating element means therein, such as a solid fuel agglomerate disclosed in our afore-mentioned Patents, or a chemical heating unit disclosed in our afore-mentioned co-pending application. The heating element means is inserted into the second container through an opening which is provided to the exterior of the entire portable heater or furnace. At least a portion of the exterior walls of this second container, and preferably a majority of the exterior walls thereof, are exposed to the interiors of the compact liquid container for heat transfer through the walls of the second container to a liquid within the compact exterior container.

A flexible liquid conduit is provided with both ends, or opposite ends, thereof connected for circulation of heated liquid from the compact liquid container through the conduit, and a positive displacement pump means is connected to or with the conduit for hand manipulation to circulate heated liquid from the compact container through the conduit on demand. The flexible liquid conduit is adapted for circulating through an appropriate piece of wearing apparel for warming thereof.

Cap means is preferably provided for closing off the opening to the interior of the second inner container, wherein the heating element is inserted. Vent means is also preferably provided in this cap to vent the interior of the second inner container to atmosphere. This permits the escape of possible accumulation of gases when using a chemical heating element, and permits the access of oxygen to the interior and proper venting in the event that the heating element is a solid fuel agglomerate.

As an added feature, this cap or cap means is also preferably provided with retainer means thereon for gripping a portion of the heating element in order to suspend the heating element within the second container. This also permits insertion of the heating element into the second container with ease.

In one form, the inner second heating chamber may take on the configuration of a tube or tube means which passes through the first-mentioned liquid container with exterior portions of the side walls of the tube exposed to the interior of the liquid container for heat transfer through the tube means to the liquid within the compact liquid container. This permits efficient heat transfer around the entire periphery of the inner container walls which are exposed to the liquid for heat transfer. A pair of cap means are provided which respectively close off opposite ends of the tube and at least one of the cap means is removable as described hereinbefore for the receipt of a heating element in the tube means. This provides a portable heater or furnace which is very inexpensive and easy to manufacture, and yet provides greater efficiency in heat exchange as more heat exchanger surface area surrounding the heating element is exposed to the liquid being heated.

BRIEF DESCRIPTION OF THE DRAWINGS

Other objects and advantages appear in the following description and claims.

The accompanying drawings show, for the purpose of exemplification without limiting the invention or the claims thereto, certain practical embodiments illustrating the principles of this invention wherein:

FIG. 2 is an enlarged view in front elevation of the furnace unit of the present invention shown in FIG. 1.

FIG. 3 is a top view of the furnace unit shown in FIG. 2.

FIG. 4 is a bottom view of the furnace unit shown in FIG. 2 with the bottom cap removed.

FIG. 5 is a view in side elevation of the furnace unit shown in FIG. 2.

FIG. 6 is a bottom view of the bottom cap shown in FIG. 2.

FIG. 7 is a view in vertical cross section of the furnace unit illustrated in FIGS. 2 through 6, and as seen along section line 7—7, of FIG. 3.

FIG. 8 is a top sectional view of the furnace unit illustrated in FIGS. 2 through 6, and as seen along section line 8—8 of FIG. 2.

FIG. 9 is an isometric view of the top cap and heating element illustrated in the furnace unit of FIG. 7.

DETAILED DESCRIPTION OF THE PREFERRED EMBODIMENT

Figure 1:
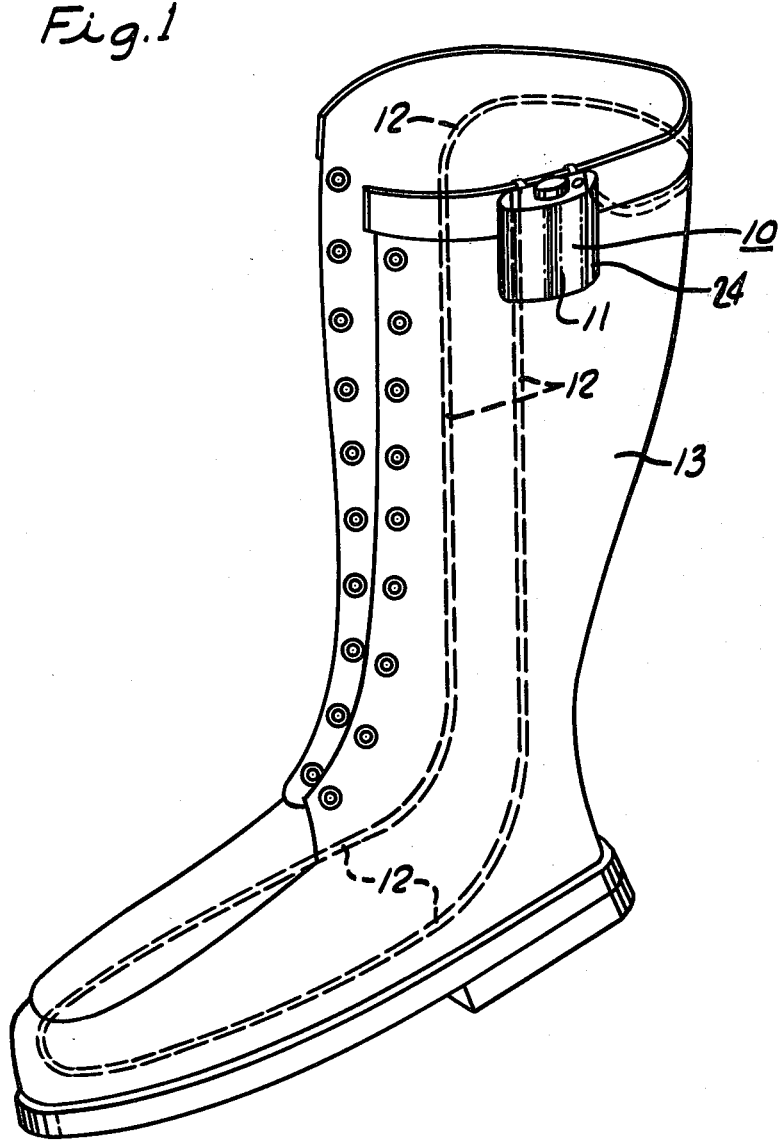
FIG. 1 is an isometric view in side elevation of the portable heater or furnace of the present invention as utilized in combination with a boot.

Referring to FIG. 1, the wearing apparel furnace or warmer 10 of the present invention is shown in combination with a boot. It may be used in combination with other wearing apparel such as socks, boot liners, gloves, etc. The warmer 10 generally consists of a portable compact heater unit or heat exchanger 11 having a liquid conduit 12 circulating throughout and within boot 13 in order to circulate heated liquid from heater unit 11. Heated liquid is pumped from unit 11 through conduit 12 by means of hand manipulated positive displacement pump 24.

Referring to FIGS. 2 through 9, the details of heater unit 11 are shown. Heater unit 11 is compact and capable of being readily carried on one's person as illustrated in FIG. 1. It includes a compact closed container 15 containing liquid 16 therein, which may be water, antifreeze, or any other suitable liquid for conducting heat. A second container 17 is received in closed container 15 with exterior portions 18 of the side walls thereof exposed to the interior of container 15 for heat transfer through the walls of inner container 17 to liquid 16. In this embodiment, second inner container 17 takes on the configuration of a tube which passes vertically through container 15. Second inner container 17 is adapted to receive heating element 19 therein. Heater element 19 is here illustrated as a solid fuel agglomerate of the type described in our afore-mentioned U.S. Patents. However, heater element 19 also represents a chemical heating unit of the type disclosed in our afore-mentioned U.S. Patent application.

A bottom cap 20 closes off the bottom end of tube 17, and a top cap 21 closes off the top of tube 17. Top cap 21 is removable for insertion of heating element 19 in tube 17. The exterior walls 18 of tube 17 are exposed for 360° therearound to the liquid 16 thereby making maximum efficient use of the heat given off by heating element 19.

Opposite ends of flexible liquid conduit 12 are connected for circulation of heated liquid 16 through conduit 12 in a closed circuit. One end of conduit 12 is connected to inlet tube 22, and the other end is connected to outlet 23. Positive displacement pump 24 is connected to conduit 12 via outlet tube 23, and the opposite or lower end of pump 24 is connected to liquid 16 or the interior of container 15 via outlet tube 25.

Positive displacement pump 24 consists of a length of flexible hose 26 connected at opposite ends to conventional ball check valves 27 and 28, such that when hose 26 is squeezed or depressed inwardly by one's fingers as indicated by arrows 29, liquid is caused to flow from the interior of outer container 15 through pump 24 and thence through conduit 12 back to the inlet 22 of container 15. The circulation of heated liquid 16 through flexible conduit 12 is regulated by the number of times pump 24 is actuated. The top of container 15 is provided with threadably removable plug 30 to provide access into the interior of container 15 to fill the same with liquid 16 and to vent off any trapped air therein.

Outer container 15 is manufactured very simply by forming the vertical side walls thereof of a single piece of sheet metal, which is soldered together as indicated at folded solder joint 31 in FIG. 8. Top and bottom end plates 32 and 33 are then soldered to this vertical wall structure. Tube 17 is a conventional metal tube which is passed through openings provided in top and bottom end walls 32 and 33 and soldered thereto to provide a seal between tube 17 and case 15.

Container 15 and inner container or tube 17 may also be constructed of other suitable materials, such as molded or extruded plastics, or extruded metals.

Top cap 21 is provided with retainer 34 on the inside thereof, which is a spring clip mechanism which grips the upper end of heater element 19 to suspend element 19 inside tube 17 when cap 21 is in position on top of tube 17 as illustrated in FIG. 7. This provides easy insertion of the heating element 19 into inner container or tube 17. When heating element 19 is a solid fuel agglomerate, the upper end thereof is inserted in spring retainer 34 and the bottom end is ignited. One then simply inserts the agglomerate into the inner container 17 by manipulating top cap 21. The bottom portion of tube 17 is provided with an annular screen 35 for catching falling ash from heating element 19 when the heating element is a slow burning solid fuel agglomerate.

Vents are provided in top cap 21 and bottom cap 20 to vent the interior of tube 17 to the exterior atmosphere. This permits the desired ingress of air to keep a solid fuel agglomerate ignited and to properly vent the interior while the agglomerate 19 is burning, or in the situation wherein the heating element 19 is a chemical unit, it is sometimes desirable to vent the interior of tube 17 where the chemical reaction of the heating unit gives off expanding gases. The vents in top cap 21 and bottom cap 20 are indicated at 36 and the size of these vents 36 is regulated by vent discs 37 which have oblong vent apertures 38 therethrough. By rotating vent discs 37, the registry of vent apertures 38 may be varied with vent apertures 36 to regulate the size of the resultant vents. Bottom cap 20 is retained in position by the bayonet lock arrangement best illustrated at the bottom of FIGS. 2 and 5.

An alternative feature is illustrated in FIG. 3, wherein a sleeve liner 40 may be inserted coaxially into tube 17 to act as a condensation barrier, or to prevent the build-up of condensation which might possibly extinguish an ignited solid fuel agglomerate. This sleeve liner 40 may take on many different desired configurations, such as a very porous or loose fibrous sleeve which will permit sufficient breathing and heat conduction therethrough, or it can take on the configuration of a metal tube with raised or embossed extensions or nubs to permit free circulation of air around the sleeve 40.

We claim:

1. A portable furnace for heating wearing apparel or the like comprising, a compact closed container for containing a liquid therein and capable of being readily carried on a person, a second container received in said closed container and adapted to receive heating element means therein through an opening to the exterior and having at least a portion of the exterior walls of said second container exposed to the interior of said compact container for heat transfer through said walls to a liquid to be contained within said compact container, a flexible liquid conduit having both ends thereof connected for circulation of heated liquid from said compact container through said conduit, and positive displacement pump means connected to said conduit for hand manipulation to circulate heated liquid from said compact container through said conduit on demand.

2. The portable furnace of claim 1, including cap means for closing off said opening.

3. The portable furnace of claim 2, said cap means including vent means therein to vent the interior of said second container to atmosphere.

4. The portable furnace of claim 2, said cap means having retainer means thereon for gripping said heating element means to suspend it in said second container.

5. A portable furnace for heating wearing apparel or the like comprising, a compact closed container for containing a liquid therein and capable of being readily carried on a person, tube means passing through said container with exterior portions of the side walls of said tube means exposed to the interior of said compact container for heat transfer through said tube means to a liquid to be contained within said compact container, a pair of cap means respectively closing off opposite ends of said tube means, at least one of said cap means being removable for the receipt of heating element means in said tube means, a flexible liquid conduit having both ends thereof connected for circulation of heated liquid from said compact container through said conduit, and pump means connected to said conduit for hand manipulation to circulate heated liquid from said compact container through said conduit on demand.

6. The portable furnace of claim 5, including vent means in at least one of said cap means to vent the interior of said tube means to exterior atmosphere.

7. The portable furnace of claim 6, wherein said heating element means is a solid fuel agglomerate.

8. The portable furnace of claim 7, one of said cap means having retainer means on the inside thereof for gripping an end of a solid fuel agglomerate to suspend a fuel agglomerate inside said tube means when said one of said cap means is in position on said tube means.

* * * * *